(12) United States Patent
Goto

(10) Patent No.: US 8,977,020 B2
(45) Date of Patent: Mar. 10, 2015

(54) IMAGE PROCESSING DEVICE AND IMAGE PROCESSING METHOD

(75) Inventor: Yoshihiro Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 228 days.

(21) Appl. No.: 13/643,603

(22) PCT Filed: Apr. 20, 2011

(86) PCT No.: PCT/JP2011/059673
§ 371 (c)(1),
(2), (4) Date: Oct. 26, 2012

(87) PCT Pub. No.: WO2011/142222
PCT Pub. Date: Nov. 17, 2011

(65) Prior Publication Data
US 2013/0039560 A1    Feb. 14, 2013

(30) Foreign Application Priority Data
May 10, 2010    (JP) ................ 2010-108109

(51) Int. Cl.
*G06K 9/00*    (2006.01)
*A61B 6/00*    (2006.01)
(Continued)

(52) U.S. Cl.
CPC ............... *A61B 6/5205* (2013.01); *A61B 8/14* (2013.01); *A61B 8/5238* (2013.01); *G06T 15/08* (2013.01); *G06T 19/00* (2013.01); *A61B 6/032* (2013.01); *A61B 6/466* (2013.01); *A61B 6/50* (2013.01); *A61B 6/504* (2013.01); *A61B 6/5211* (2013.01);
(Continued)

(58) Field of Classification Search
USPC .................................. 382/128–134
See application file for complete search history.

(56) References Cited

U.S. PATENT DOCUMENTS 6,226,418 B1 *   5/2001   Miller et al. .................. 382/294
2002/0090119 A1 *  7/2002   Saito et al. .................... 382/128
(Continued)

FOREIGN PATENT DOCUMENTS

| CN | 101069655 | 11/2007 |
|---|---|---|
| JP | 2002-150313 | 5/2002 |

(Continued)

OTHER PUBLICATIONS

International search report in corresponding PCT/JP2011/059673.

*Primary Examiner* — Alex Liew
(74) *Attorney, Agent, or Firm* — Cooper & Dunham LLP

(57) ABSTRACT

An image processing device 100 divides a hollow organ 50 extracted from a volume image 40 using a plurality of planes 20 including an arbitrary eye vector 23 or a plurality of planes along the centerline of the hollow organ 50, transforms the coordinates of a point inside the hollow organ 50 along a predetermined convex surface set outside the hollow organ 50 on each plane 20, and gives a pixel value of an original position to a corresponding point after the coordinate transformation. Then, a folded volume image is generated by combining the respective planes 20 in a reverse procedure of the division procedure, and a shaded folded three-dimensional image 90 is generated by projecting the folded volume image to a projection surface from the arbitrary viewing direction and is displayed on a display device 107.

14 Claims, 7 Drawing Sheets

(51) Int. Cl.
  *A61B 8/14*      (2006.01)
  *A61B 8/08*      (2006.01)
  *G06T 15/08*     (2011.01)
  *G06T 19/00*     (2011.01)
  *A61B 6/03*      (2006.01)
  *G06T 7/60*      (2006.01)
  *A61B 5/055*     (2006.01)
  *A61B 5/00*      (2006.01)

(52) U.S. Cl.
  CPC ............... *A61B 5/055* (2013.01); *A61B 5/4255* (2013.01); *G06T 2219/008* (2013.01); *G06T 2219/2021* (2013.01); *G06T 7/606* (2013.01); *G06T 2207/30172* (2013.01); *G06T 2207/10072* (2013.01); *G06T 2207/30028* (2013.01)
  USPC ........... 382/128; 382/129; 382/130; 382/131; 382/132; 382/133; 382/134

(56) References Cited

U.S. PATENT DOCUMENTS

| | | | |
|---|---|---|---|
| 2004/0161144 A1* | 8/2004 | Barth | 382/154 |
| 2005/0113680 A1* | 5/2005 | Ikeda et al. | 600/425 |
| 2005/0163356 A1* | 7/2005 | Makram-Ebeid et al. | 382/128 |
| 2007/0182731 A1 | 8/2007 | Gundel | |
| 2009/0080746 A1* | 3/2009 | Xu et al. | 382/131 |
| 2010/0074487 A1* | 3/2010 | Miyamoto et al. | 382/128 |
| 2010/0098313 A1* | 4/2010 | Knapp et al. | 382/132 |
| 2010/0201683 A1 | 8/2010 | Shirahata et al. | |
| 2013/0104086 A1* | 4/2013 | Mlyniec et al. | 715/849 |

FOREIGN PATENT DOCUMENTS

| | | |
|---|---|---|
| JP | 2010-17490 | 1/2010 |
| WO | WO2008/111316 | 9/2008 |
| WO | WO2009/016927 | 2/2009 |
| WO | WO2010/010880 | 1/2010 |

* cited by examiner

PIXEL VALUE OF P(X1, Y1) IS USED FOR PIXEL VALUE OF Q(X, Y)

$$X1 = X0 - (2\pi - \theta - \pi/2) \cdot r0$$
$$Y1 = Y0 - r0 - r$$

$$X = X0 + (r + r0) \cdot \cos\theta$$
$$Y = Y0 + (r + r0) \cdot \sin\theta$$

IMAGE PROCESSING DEVICE AND IMAGE PROCESSING METHOD

TECHNICAL FIELD

The present invention relates to an image processing device and an image processing method of generating a three-dimensional image from a plurality of tomographic images.

BACKGROUND ART

Conventionally, a method of generating a three-dimensional image of an object using a group of a series of tomographic images scanned by, for example, an X-ray CT (computed tomography) apparatus, an MRI (magnetic resonance imaging) apparatus, or an ultrasonic diagnostic apparatus is known. For example, PTL 1 discloses an image display device that generates and displays an inside-out image, which is obtained when the inside surface of an organ is turned over to the outer surface, by extracting the contour of a hollow organ from a medical image constructed by scanning the hollow organ, setting a radial line from the radiation center set inside the hollow organ towards the contour of the lumen, and copying a pixel value of a point inside the hollow organ onto the radial line outside a contour point.

In addition, PTL 2 discloses a three-dimensional image construction method capable of checking the irregularities inside an object from the outside by generating a two-dimensional image by a perspective transformation of a volume image, which is formed by stacking tomographic images of the object, to a coordinate system on an arbitrary perspective plane, calculating a distance between a position of a virtual linear light source set inside the object and an inside contour point of the object, and reflecting the distance in the shading of the two-dimensional image. In addition, PTL 3 discloses a medical image processing device that displays an image, which has a central portion in which a virtual endoscopic image equivalent to an image observed with an endoscope is displayed and a peripheral portion in which the inside of a hollow organ is spread, for example, by setting a viewpoint inside the hollow organ and setting the projection directions in different directions in the central portion and the peripheral portion of a projection plane.

CITATION LIST

Patent Literature

[PTL 1] JP-A-2010-17490
[PTL 2] JP-A-9-237352
[PTL 3] JP-A-2009-22411

SUMMARY OF INVENTION

Technical Problem

As described above, there are various techniques of generating an image showing the inside of an object outside.

However, in order to make the irregularities of the inner surface or portions hidden in plicae observable more easily, it is preferable to be able to change the shape of the surface of an organ even on the image as if the surface is spread by pressing from the back side of the organ using fingers. In addition, when deforming a portion to be observed, the portion may become an image far from the original shape or position. Since this interferes with understanding rather, it is preferable to display the original shape or position so as to be able to be understood intuitively.

The present invention has been made in view of the above-described problems, and it is an object of the present invention to provide an image processing device and an image processing method capable of generating and displaying a folded image, in which a part of the inner surface of a hollow organ is exposed outside, by changing the shape of the hollow organ to a shape in which sleeves of clothes are folded.

Solution to Problem

In order to achieve the object described above, the present invention is an image processing device characterized in that it includes: a coordinate transformation unit that performs coordinate transformation so as to fold each point inside a hollow organ, which is extracted from a volume image formed by stacking a plurality of tomographic images, along a predetermined convex surface set outside the hollow organ and gives a pixel value of an original position to a corresponding point after the coordinate transformation; and a generation unit that generates a folded volume image using image information after the coordinate transformation by the coordinate transformation unit.

In addition, the present invention is an image processing method characterized in that it includes a coordinate transformation step of performing a coordinate transformation so as to fold each point inside a hollow organ, which is extracted from a volume image formed by stacking a plurality of tomographic images, along a predetermined convex surface set outside the hollow organ and giving a pixel value of an original position to a corresponding point after the coordinate transformation; and a generation step of generating a folded volume image using image information after the coordinate transformation in the coordinate transformation step.

Advantageous Effects of Invention

By the image processing device and the image processing method of the present invention, it is possible to generate and display a folded image, in which a part of the inner surface of a hollow organ is exposed outside, by changing the shape of the hollow organ to a shape in which sleeves of clothes are folded.

DESCRIPTION OF EMBODIMENTS

Hereinafter, embodiments of the present invention will be described in detail on the basis of the drawings.

First, the configuration of an image processing system 1 to which an image processing device 100 of the present invention is applied will be described with reference to FIG. 1.

Figure 1:
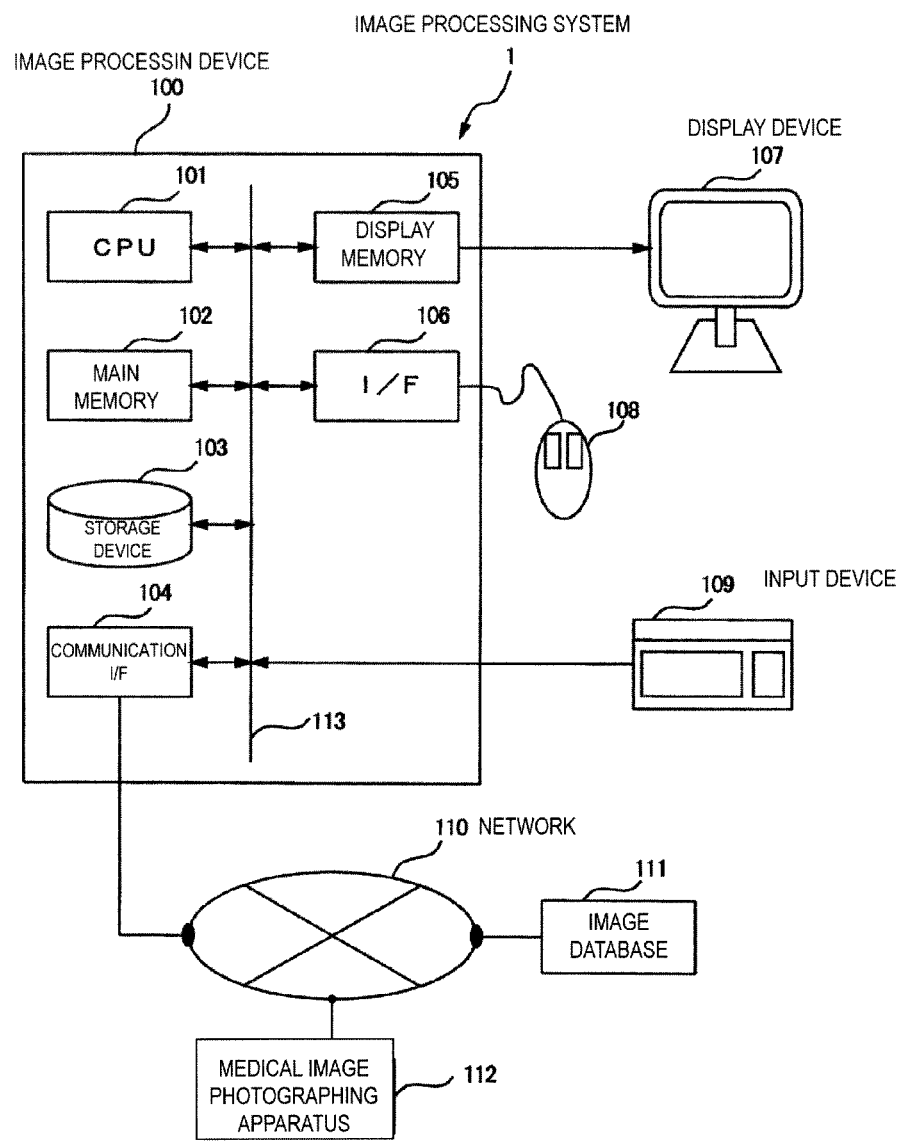
FIG. 1 is a view showing the overall configuration of an image processing device 100.

As shown in FIG. 1, the image processing system 1 includes: the image processing device 100 having a display device 107 and an input device 109; an image database 111 connected to the image processing device 100 through a network 110; and a medical image scanning apparatus 112.

The image processing device 100 is a computer which performs processing, such as image generation and image analysis. For example, a medical image processing device installed in a hospital and the like is included.

As shown in FIG. 1, the image processing device 100 includes a CPU (Central Processing Unit) 101, a main memory 102, a storage device 103, a communication interface (communication I/F) 104, a display memory 105, and an interface (I/F) 106 with an external device such as a mouse 109, and the respective units are connected to each other through a bus 113.

The CPU 101 loads a program stored in the main memory 102 or the storage device 103 to a work memory region on a RAM of the main memory 102 and executes the program and performs driving control of the respective units connected to each other through the bus 113, thereby realizing various kinds of processing performed by the image processing device 100.

In addition, the CPU 101 executes a folded image generation process (refer to FIG. 2), which will be described later, to generate a folded three-dimensional image 90 and displays it on the display device 107. The folded three-dimensional image 90 and the folded image generation process will be described later.

The main memory 102 is configured to include a ROM (Read Only Memory), a RAM (Random Access Memory), and the like. The ROM permanently holds a boot program of a computer, a program such as BIOS, data, and the like. In addition, the RAM temporarily holds a program, data, and the like loaded from the ROM, the storage device 103, and the like, and has a work area used when the CPU 101 performs various kinds of processing.

The storage device 103 is a storage device which performs reading/writing of data from/into a HOD (hard disk drive) or other recording media. Programs executed by the CPU 101, data required to execute the programs, an OS (operating system), and the like are stored in the storage device 103. As programs, a control program equivalent to an OS and application programs are stored. Each of program codes thereof is read by the CPU 101 when necessary and moved to the RAM of the main memory 102, thereby being executed as various kinds of means.

The communication I/F 104 has a communication control device, a communication port, and the like, and mediates communication between the image processing device 100 and the network 110. In addition, the communication I/F 104 performs communication control with the image database 111, other computers, or the medical image scanning apparatus 112, such as an X-ray CT apparatus or an MRI apparatus, through the network 110.

The I/F 106 is a port for connection with a peripheral device and performs transmission and reception of data to and from the peripheral device. For example, a pointing device, such as the mouse 108 or a stylus pen, maybe connected through the I/F 106.

The display memory 105 is a buffer which temporarily accumulates display data input from the CPU 101. The accumulated display data is output to the display device 107 at a predetermined timing.

The display device 107 is formed by a display device such as a liquid crystal panel or a CRT monitor, and a logic circuit which cooperates with the display device to execute display processing, and is connected to the CPU 101 through the display memory 105. The display device 107 displays the display data accumulated in the display memory 105 under control of the CPU 101.

The input device 109 is an input device such as a keyboard, and outputs to the CPU 101 various kinds of instructions or information input by an operator. The operator operates the image processing device 100 interactively using the display device 107, the input device 109, and an external device such as the mouse 108.

The network 110 includes various communication networks, such as a LAN (Local Area Network), a WAN (Wide Area Network), an intranet, and the Internet, and mediates communication connection between the image database 111, a server, or other information devices and the image processing device 100.

The image database 111 accumulates and stores image data obtained by the medical image scanning apparatus 112. Although the image processing system 1 shown in FIG. 1 has a configuration in which the image database 111 is connected to the image processing device 100 through the network 110, the image database 111 may be provided, for example, in the storage device 103 of the image processing device 100.

Next, the operation of the image processing device 100 will be described with reference to FIGS. 2 to 6. The CPU 101 of the image processing device 100 reads from the main memory 102 a program and data regarding the folded image generation process shown in FIG. 2 and executes the process on the basis of the program and data.

Figure 3:
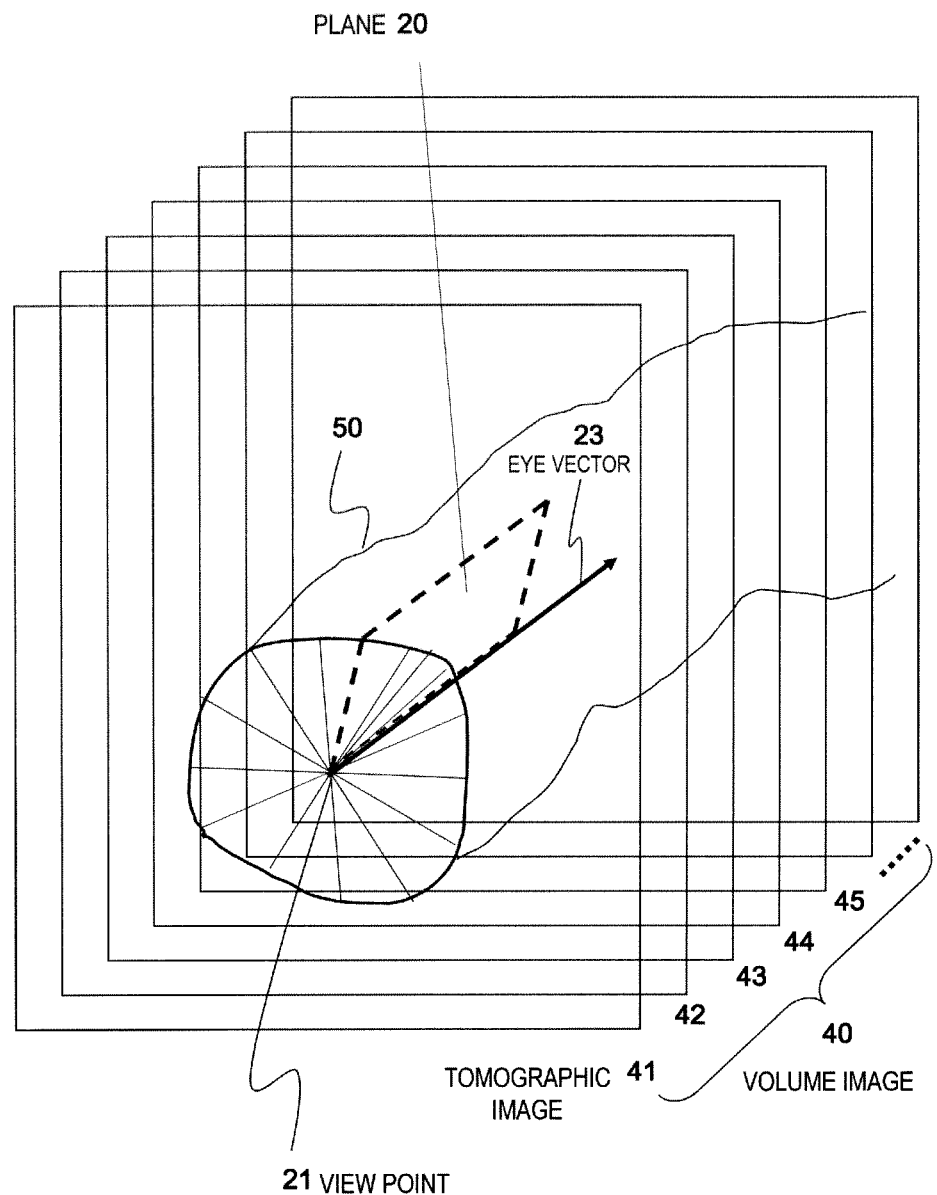
FIG. 3 is a view illustrating an example of dividing a hollow organ 50 in a volume image 40 using a plane 20.

In addition, it is assumed that data of a volume image 40 to be calculated is acquired from the image database 111 or the like through the network 110 and the communication I/F 104 and stored in the storage device 103 of the image processing device 100 at the start of execution of the following processing. The volume image 40 is image data formed by stacking a plurality of tomographic images 41, 42, 43, ..., as shown in FIG. 3. Each pixel (voxel) of the volume image 40 has a pixel value.

Figure 2:
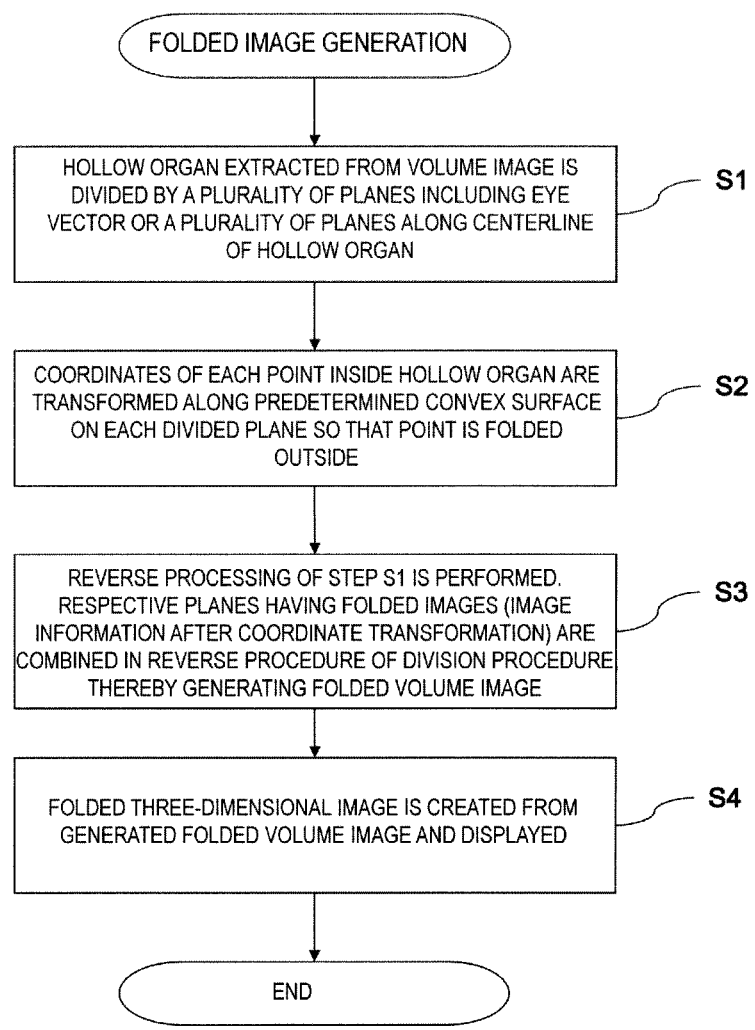
FIG. 2 is a flow chart illustrating the flow of a folded image generation process executed by the image processing device 100 related to the present invention.

In the folded image generation process shown in FIG. 2, the CPU 101 of the image processing device 100 first reads the volume image 40, which is formed by stacking the series of tomographic images 41, 42, ... obtained by scanning a target region, as input image data. The volume image 40 read herein is a group of a series of tomographic images of a region including a hollow organ 50 such as the colon. As appropriate examples of the input image data, an ultrasonic image, a CT image, or an MR image may be described. In addition, the target region is not limited to the colon, and may be other hollow organs, for example, blood vessels or bronchi.

First, the CPU 101 sets an arbitrary viewpoint 21 inside the hollow organ 50 extracted from the volume image 40 and divides the hollow organ 50 by a plurality of planes including an arbitrary eye vector 23 set inside the hollow organ 50 or a plurality of planes along the centerline of the hollow organ 50 (step S1). In the following explanation, the plane which divides the hollow organ 50 is called a plane 20.

In the case of generating a virtual endoscopic image finally as in the present embodiment, the above-described view point 21 is preferably a view point of the virtual endoscopic image. The eye vector 23 is set from the view point 21 toward an arbitrary direction in the depth direction of the hollow organ 50.

The centerline of the hollow organ 50 is a line formed by connecting the coordinates of the center of gravity of each cross section of the hollow organ 50 along the hollow organ 50. The coordinates of the center of gravity can be calculated using the coordinates of a wall (boundary between an organ region and other regions) of the hollow organ.

FIG. 3 is a view showing an example of division by the plane 20 including the eye vector 23 of the hollow organ 50.

As shown in FIG. 3, the arbitrary view point 21 is set inside the hollow organ 50 in the volume image 40, and the eye vector 23 is set in the depth direction of the hollow organ 50. The hollow organ 50 is divided by the plurality of planes 20 including the eye vector 23. The hollow organ 50 is divided radially by the plurality of planes 20 with the view point 21 as the center.

Figure 4:
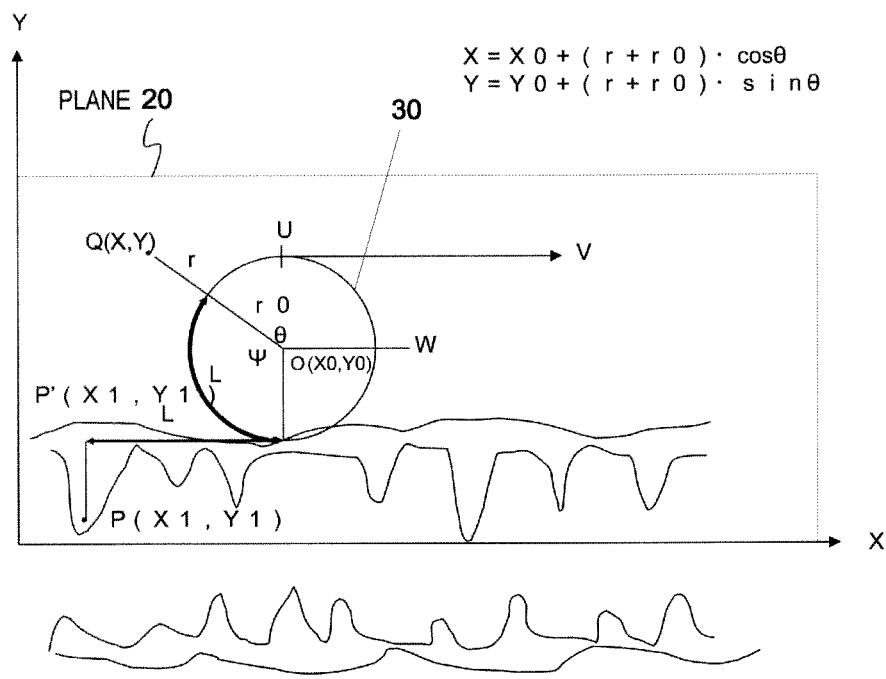
FIG. 4 is a view showing the matching of the coordinates when folding the hollow organ 50 along the convex surface (a circle 30) (when performing coordinate transformation).

As shown in FIG. 4, each plane 20 which divides the hollow organ 50 has image information of the wall, inside region, and outside region of the hollow organ 50.

In addition, FIG. 4 is an example where the X axis of the plane 20 and the eye vector 23 match each other. When the plane 20 is a region shown by a dotted line in FIG. 3, a lower part of the X axis in FIG. 4 is not included in the plane 20. However, the lower part of the X axis in FIG. 4 is included in other planes which divide the hollow organ 50. In addition, as shown in FIG. 4, the hollow organ 50 may be divided so that upper and lower parts of the X axis are included in the same plane.

Then, the CPU 101 transforms the coordinates of each point inside the hollow organ 50 using each divided plane 20 so that the point is folded outside (step S2). That is, the CPU 101 calculates a corresponding point when folding each point inside the hollow organ 50 along a predetermined convex surface, which is set outside the hollow organ 50, on each divided plane 20 and gives a pixel value of the original position to the calculated corresponding point.

Referring to FIG. 4, coordinate transformation processing of step S2 will be described.

As shown in FIG. 4, on the plane 20 including the eye vector 23, a direction of the eye vector 23 is an X direction and a direction perpendicular to the eye vector 23 is a Y direction. In addition, the predetermined convex surface is set outside the hollow organ 50. In the example shown in FIG. 4, a circle 30 with a radius r0 is set as the convex surface, and the circle 30 is set so as to be adjacent to the outer surface of the hollow organ 50.

The CPU 101 transforms the coordinates of each point P(X1, Y1) inside the hollow organ 50 along the convex surface (circle 30).

For example, when folding the point P(X1, Y1), which is located inside the hollow organ 50 by a distance r from a point P'(X1, Y1') on the surface of the hollow organ 50, along the circle 30, the point P(X1, Y1) is moved by a distance L along the circumference of the circle 30, and a point Q separated from the point by the distance r in the normal direction of the circle 30 is set as the corresponding point after the coordinate transformation. The above-described distance L is a distance between a contact point R of the circle 30 and the hollow organ 50 and the point P'.

The coordinates of the corresponding point Q(X, Y) of the point P(X1, Y1) inside the hollow organ 50 are calculated from the following Expressions.

$X1 = X0 - L = X0 - \Psi \cdot r0 = X0 - (2\pi - \theta - \pi/2) \cdot r0$ $Y1 = Y0 - r0 - r$ $X = X0 + (r + r0) \cdot \cos\theta$ $Y = Y0 + (r + r0) \cdot \sin\theta$ Here, (X0, Y0) is the coordinates of a center 0 of the circle 30, θ is an angle between a straight line 0W extending in the positive direction of the X axis from the center 0 of the circle 30 and a straight line 0Q, r0 is the radius of the circle 30, and r is the distance from the point P to the surface of the hollow organ 50.

A pixel value of the original point P(X1, Y1) is assigned to a pixel value of the corresponding point Q(X, Y), and an image (a folded image 80) after the coordinate transformation is obtained.

Figure 5:
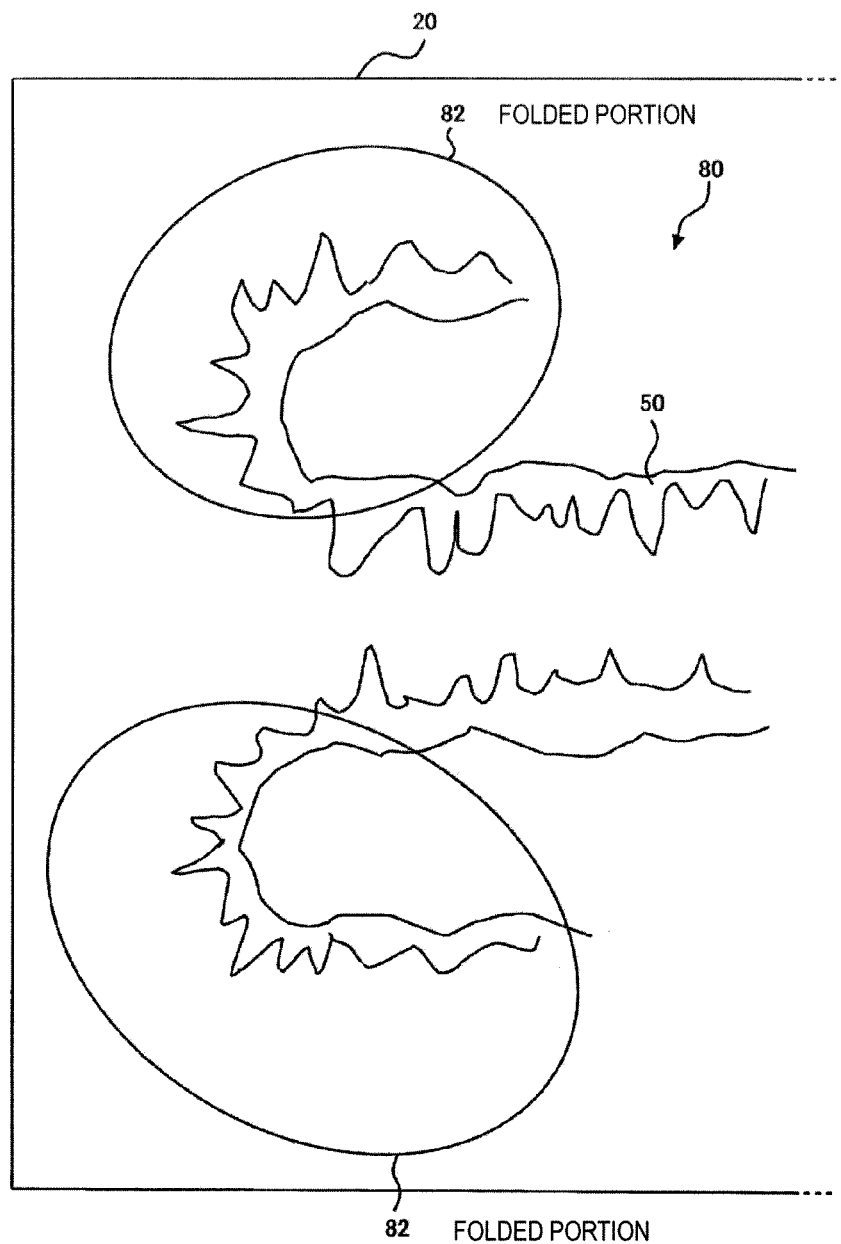
FIG. 5 is an example of a folded image 80 of the hollow organ 50 on the plane 20.

As shown in FIG. 5, in a folded portion 82 of the folded image 80 formed on the plane 20, the corresponding point Q is calculated more coarsely as a distance of a pixel from the circle 30 increases since the coordinates of each point P inside the hollow organ 50 are transformed along the convex surface (circle 30). For this reason, the CPU 101 calculates pixel values other than the corresponding point Q by interpolating the pixel value of the peripheral corresponding point Q.

In addition, when virtual endoscopic display of the folded hollow organ 50 is performed in step S4 described later, a range of the coordinate transformations (range of the point P whose the corresponding point Q is calculated) maybe limited to the point P in a range from the distance between the points P' and R in FIG. 4 of L=0 (contact point between the hollow organ 50 and the circle 30) to L=π·r0 (half circumference of the circle 30). This is because a range farther than L=π·r0 is located on the rear side of the circle 30 and does not appear on the virtual endoscopic image at the time of the virtual endoscopic display in step S4 described later.

In addition, when calculating the corresponding point Q of the point P in the range of L>π·r0, the corresponding point Q may be calculated along the circle 30 for the range of up to L=π·r0 and a straight line UV parallel to the X axis for the range exceeding L=π·r0.

When the coordinate transformation is performed as in step S2, for example, the folded image 80 shown in FIG. 5 is obtained.

As shown in FIG. 5, in the folded portion 82 in which the hollow organ 50 has been deformed into a shape in which sleeves of clothes are rolled up, the inside of the hollow organ 50 is exposed outward. Since the folded portion 82 is deformed into the shape along the convex surface (circle 30), plicae in the folded portion 82 are spread. Accordingly, a portion hidden behind the plicae can easily be observed.

Then, the CPU 101 performs reverse processing of step S1. That is, the respective planes 20 having image information of the folded image 80 are combined in the reverse procedure of step S1, thereby obtaining a folded volume image (step S3).

The CPU 101 creates a folded three-dimensional image 90 from the folded volume image (step S4). The folded three-dimensional image 90 created herein may be any of a shaded three-dimensional image, a stereoscopic image, and the like.

The shaded three-dimensional image is an image viewed in a three-dimensional manner by setting an arbitrary view point and an arbitrary eye vector and performing predetermined shading on each pixel of a two-dimensional image obtained by projecting the volume image to the projection plane. Any of a volume rendering method, a ray casting method, a surface method, a depth method, and the like may be used as a shading method. In addition, the projected image may be either a parallel projection image or a central projection image. When performing central projection by setting a view point inside the hollow organ 50 and setting an eye vector in the depth direction of the lumen, it is possible to obtain a virtual endoscopic image as when the hollow organ 50 is observed with an endoscope (refer to FIG. 6). The stereoscopic image is intended to achieve a stereoscopic image in an observer's brain by generating binocular parallax intentionally. A stereoscopic image using a lenticular lens or a stereoscopic image using a parallax barrier is known (JP-A-2004-78086 and the like).

Figure 6:
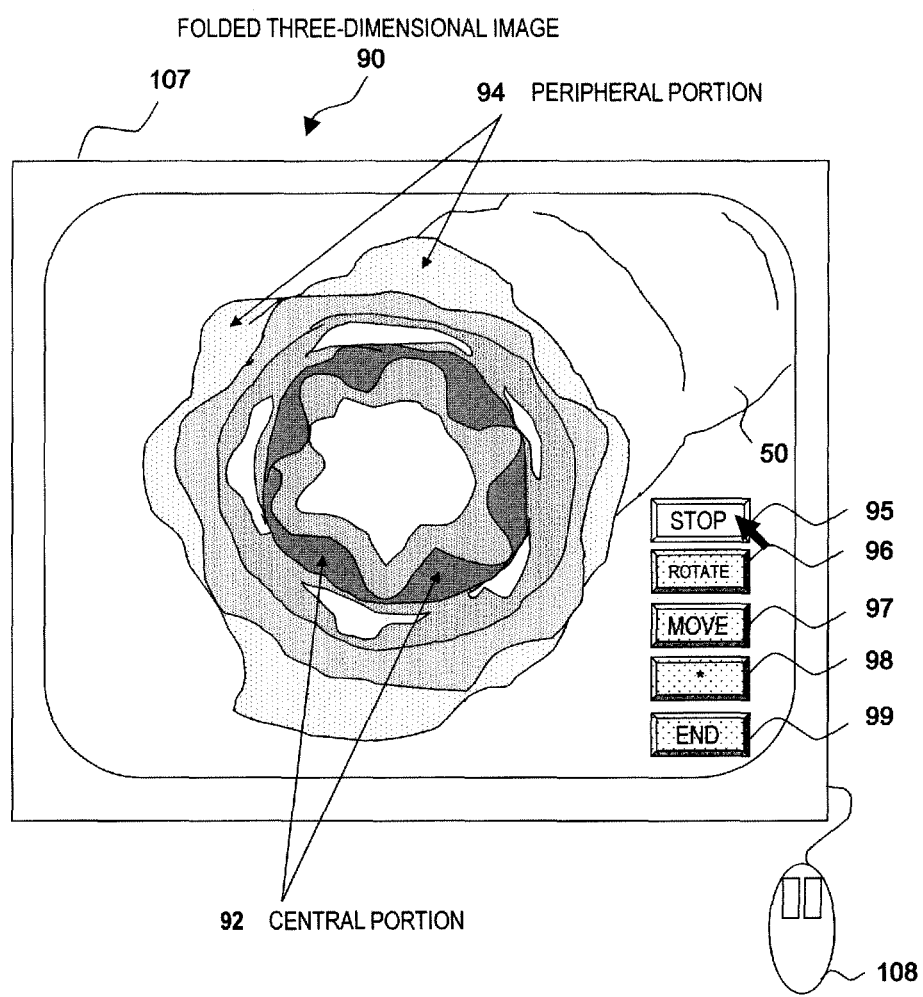
FIG. 6 is an example of a folded three-dimensional image 90 which is displayed in a three-dimensional manner like an endoscopic image.

FIG. 6 is an example of the folded three-dimensional image 90 under the virtual endoscopic display. When the virtual endoscopic display of a folded volume image in which a part of the hollow organ 50 is folded is performed, a normal virtual endoscopic image is displayed in a central portion 92 of the image 90 and the folded portion 82 is displayed on a peripheral portion 94 of the image 90, as shown in FIG. 6. Inside plicae of the hollow organ 50 are displayed in the central portion 92 of the image 90 without being folded, while the inside plice of the hollow organ 50 are displayed in the peripheral portion 94 so as to be exposed outward.

Thus, the hollow organ 50 is folded as if the sleeves of clothes are rolled up and as a result, the inside plicae are spread and displayed in a part of the image (in the case of the virtual endoscopic image, displayed in the peripheral portion 94 of the image). For this reason, the inside of the hollow organ 50 in the folded portion 82 can easily be observed. In addition, since the coordinate transformation of the folded portion 82 is performed along the convex surface (circle 30), the folded portion 82 is deformed as if the inner surface is pressed and spread by pressing from the back side (outside of the hollow organ 50) using fingers. As a result, a portion hidden behind the plicae expands and can easily be observed. In addition, since portions other than the folded portion 82 are displayed in the same manner as a normal three-dimensional image (in the case of the virtual endoscopic image, a central portion of the image becomes a normal endoscopic image), the portions can be observed with the same sense as in the image diagnosis that a doctor or the like usually performs. Accordingly, it becomes easy to intuitively grasp the original position or the original shape of an observed portion.

In addition, a display state of the folded three-dimensional image 90 may be changed according to a predetermined order or the operation of the operator.

For example, as shown in FIG. 6, a stop button 95, a rotation button 96, a move button 97, a surface deformation button 98, and an end button 99 which are operated by the user are provided, and the CPU 101 changes the display state of the folded three-dimensional image 90 in response to a clicking operation of each button.

Examples of the display state include not only a stop display mode specified instep S4 but also a rotational display mode, a moving display mode, and a surface deformation mode.

In the rotational display mode, the direction of the eye vector 23 under the virtual endoscope display is changed. The direction of the eye vector 23 is changed according to a setting operation. The CPU 101 generates a folded three-dimensional image 90 by executing the above-described folded image generation process on the basis of the changed eye vector 23 and displays the folded three-dimensional image 90.

In the moving display mode, the CPU 101 generates a plurality of the folded three-dimensional images 90 by calculating the corresponding point Q of the point P within a predetermined range (performing the coordinate transformation in step S2) while moving the circle 30 (convex surface) sequentially along the hollow organ 50 and displays the plurality of folded three-dimensional images 90 sequentially like moving images.

Therefore, since the folded three-dimensional images 90 can be displayed sequentially while moving the folded position of the hollow organ 50 in the depth direction, it becomes easy to observe the entire hollow organ.

In the surface deformation mode, the CPU 101 generates the plurality of folded three-dimensional images 90 with different surface shapes at the folded positions by calculating the corresponding point Q by changing the shape of the convex surface used for folding (performing the coordinate transformation instep S2) and displays the plurality of folded three-dimensional images 90 sequentially. For example, the folded three-dimensional image 90 is generated by changing a value of the radius of the circle 30, or the folded three-dimensional image 90 along an arbitrary curve such as an ellipse, a parabola, or a hyperbola, a triangle, a rectangle, and other polygons instead of the circle 30 is generated. In this manner, it is possible to display the plurality of various folded three-dimensional images 90 of different plica spreading methods or different viewing angles.

In addition, display states of the stop display mode, the rotational display mode, the moving display mode, and the surface deformation mode may be appropriately combined and displayed.

When an end instruction is input by operating the end button 99, the series of folded image generation processes are ended.

In addition, the folded three-dimensional image 90 may be displayed together with a scale added in the circumferential direction.

Figure 7:
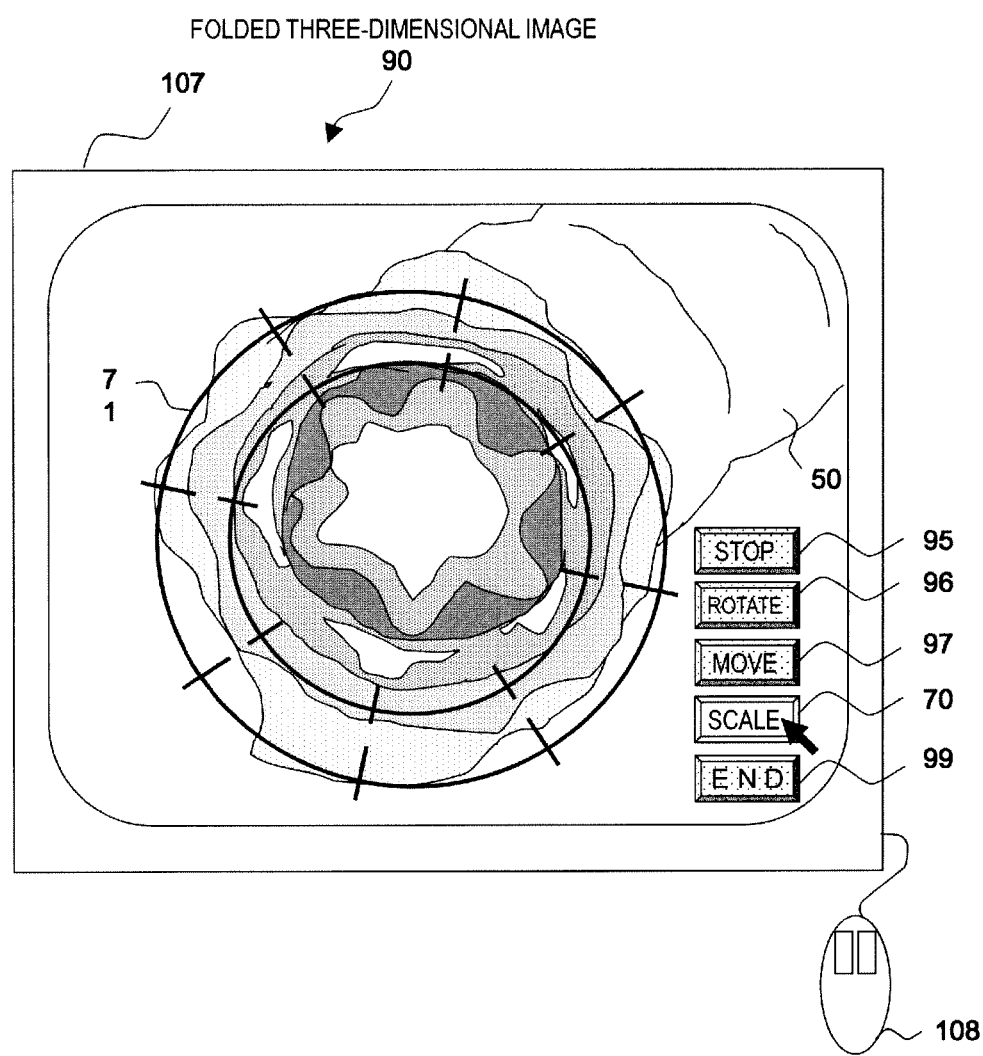
FIG. 7 is a display example in which a scale is added to the folded three-dimensional image 90.

For example, as shown in FIG. 7, scales 71 in which scale marks indicating distances in the circumferential direction inside the hollow organ are added on the circumference of an ellipse are displayed in folded portions of the folded three-dimensional image 90 so as to overlap each other. Although two scales 71 are arranged in the radial direction and displayed in the example shown in FIG. 7, the number of displayed scales 71 is not limited to two.

The ellipticity of the scale 71 may be changed according to the viewing direction or the position of the view point. That is, when the viewing direction is parallel to the depth direction of the hollow organ or when the position of the view point is on the centerline of the hollow organ, the ellipse may be made similar to a true circle. On the other hand, the ellipticity may be made to increase as the inclination of the viewing direction and the depth direction of the hollow organ increases and as a distance of the position of the view point from the centerline of the hollow organ increases.

Since the inside of the hollow organ 50 expands outward in the folded portion, the distance between the scale marks on the circumference of the ellipse is increased by the outside scale. In addition, the distance between the scale marks may be changed according to the shape of the folded portion. For example, the distance between the scale marks maybe increased in the folded portion which is more pressed and spread.

The position of the scale mark of the scale 71 may be matched to the position of the plane when the hollow organ 50 is divided in step S1 or to the middle of the adjacent planes. In this manner, the operator can know the position of the pixel value calculated by interpolation.

Switching of display and non-display of the scale 71 is performed when the operator performs an operation of clicking on a scale button 70 displayed on the display device 107.

By displaying the scale 71 on the folded three-dimensional image 90 so as to overlap each other, the operator can see the size of the folded portion displayed in a deformed state while comparing it with other portions.

As described above, the image processing device 100 of the present invention divides the hollow organ 50, which is extracted from the volume image 40 formed by stacking the plurality of tomographic images, using the plurality of planes 20 including the arbitrary eye vector 23 set in the depth direction of the hollow organ or the plurality of planes along the centerline of the hollow organ and deforms the divided portions along the predetermined convex surface (for example, the circle 30), which is set outside the hollow organ 50, on each plane 20. That is, the CPU 101 calculates the corresponding point Q when folding each point P in a predetermined range inside the hollow organ 50 along the convex surface (circle 30) and gives the pixel value of the original position to the corresponding point Q. The respective planes 20 on which the coordinate-transformed image is placed as described above are combined in a reverse procedure of the division procedure, thereby generating the folded volume image. Then, the shaded folded three-dimensional image 90 is generated by projecting the folded volume image to the projection plane from the arbitrary viewing direction, and is displayed on the display device 107.

Therefore, since the hollow organ 50 is folded as if the sleeves of clothes are rolled up and accordingly the inside plicae are displayed outside, it becomes easy to observe the inside the hollow organ 50. In addition, since the hollow organ 50 is folded along the convex surface, portions hidden behind the plicae are spread and displayed. Accordingly, the portions hidden behind the plicae can easily be observed. In addition, the plicae behind folded portion are displayed near the image of the normal hollow organ 50. Since the position or the shape before folding can easily be grasped intuitively, this is effective for diagnosis of a doctor or the like.

In addition, the above-described convex surface may be either an arbitrary curved surface or an arbitrary polygon including a circle or an ellipse adjacent to the outer surface of the hollow organ 50. If an appropriate convex surface is selected according to the state of the plicae of the inner surface, it is possible to generate the folded three-dimensional image that can easily be observed.

In addition, the folded three-dimensional image 90 may be displayed in various display formats as well as the virtual endoscope display in the example described above. For example, the moving display mode is preferred in which the plurality of folded three-dimensional images 90 are generated by transforming the coordinates of each point inside the hollow organ 50 along the above-described convex surface while moving the convex surface sequentially along the outer surface of the hollow organ and the plurality of folded three-dimensional images 90 are displayed sequentially like moving images. In the moving display mode, the folded image can be displayed such that movement in the depth direction is made while folding the hollow organ 50 sequentially. Therefore, it becomes easy to observe the entire hollow organ.

In addition, the surface deformation mode is preferred in which the plurality of folded three-dimensional images 90 with different surface shapes at the folded positions are generated by transforming the coordinates of each point inside the hollow organ 50 along the above-described convex surface by changing the shape of the convex surface sequentially or according to the operation of the operator and the plurality of folded three-dimensional images 90 are displayed sequentially.

In the surface deformation mode, the shape of the folded portion is changed to various shapes. Therefore, it is possible to display the plurality of folded three-dimensional images 90 of different fold spreading methods or different viewing angles.

In addition, the folded volume image may be generated by projecting the pixel value of the hollow organ to the trumpet-shaped curved surface.

Although the preferred embodiments of the image processing device related to the present invention have been described with reference to the accompanying drawings, the present invention is not limited to such examples. It is apparent to those skilled in the art that various changes and modifications can be made within the range of the technical idea disclosed in this specification, and it should undoubtedly be understood that they also belong to the technical range of the present invention.

REFERENCE SIGNS LIST

1: image processing system
100: image processing device
101: CPU
102: main memory
103: storage device
104: communication I/F
105: display memory
106: I/F
107: display device
108: mouse
109: input device
20: plane including an eye vector or plane along the centerline of a hollow organ
30: circle
40: volume image
41, 42, . . . : tomographic image
50: hollow organ
80: image formed by folding a point inside the hollow organ 50 on the plane 20
82: folded portion
90: folded three-dimensional image under virtual endoscopic display
92: central portion of the folded three-dimensional image 90
94: peripheral portion of the folded three-dimensional image 90
95: stop button
96: rotation button
97: move button
98: surface deformation button
99: end button
P: point inside a hollow organ
Q: corresponding point after coordinate transformation
R: contact point of the circle 30 and the hollow organ 50

The invention claimed is:

1. An image processing device comprising:
a coordinate transformation unit that sets a predetermined convex curved surface to an outside of a hollow organ, performs coordinate transformation so as to fold each point inside the hollow organ, which is extracted from a volume image formed by stacking a plurality of tomographic images, along the predetermined convex curved surface and gives a pixel value of an original position to a corresponding point after the coordinate transformation; and
a generation unit that generates a folded volume image using image information after the coordinate transformation by the coordinate transformation unit.

2. The image processing device according to claim 1, further comprising:
a division unit that divides a region of the hollow organ using a plurality of planes including an arbitrary eye vector set in a depth direction of the hollow organ or a plurality of planes along a centerline which is formed by connecting the coordinates of the center of gravity of each cross section of the hollow organ,
wherein the coordinate transformation unit performs the coordinate transformation on each plane divided by the division unit, and
the generation unit generates the folded volume image by combining the respective planes having he image information after the coordinate transformation.

3. The image processing device according to claim 1, further comprising:
a display unit that generates a folded three-dimensional image by projecting the folded volume image generated by the generation unit from an arbitrary viewing direction and displays the folded three-dimensional image.

4. The image processing device according to claim 3.
wherein a range for the coordinate transformation of the coordinate transformation unit is limted according to the folded three-dimensional image displayed on the display unit.

5. The image processing device according to claim 1,
wherein the convex curved surface is at least one of a circle, an ellipse and an arbitrary curved surface which are adjacent to an outer surface of the hollow organ.

6. The image processing device according to claim 3, further comprising:
a three-dimensional moving image display unit that generates a plurality of the folded three-dimensional images by performing the coordinate transformation using the coordinate transformation unit while moving the convex surface sequentially along an outer surface of the hollow organ and displays the plurality of folded three-dimensional images sequentially.

7. The image processing device according to claim 3, further comprising:
a surface deformation display unit that generates a plurality of the folded three-dimensional images with different surface shapes at folded positions by performing the coordinate transformation using the coordinate transformation unit by changing the shape of the convex surface sequentially or according to an operation of an operator and displays the plurality of folded three-dimensional images sequentially.

8. An image processing method comprising:
a coordinate transformation step of setting a predetermined convex curved surface to an outside of a hollow organ, performing coordinate transformation so as to fold each point inside the hollow organ, which is extracted from a volume image formed by stacking a plurality of tomographic images, along the predetermined convex curved surface and giving a pixel value of an original position to a corresponding point after the coordinate transformation; and
a generation step of generating a folded volume image using image information after the coordinate transformation in the coordinate transformation step.

9. The image processing method according to claim 8, further comprising:
a division step of dividing a region of the hollow organ using a plurality of planes including an arbitrary eye vector set in a depth direction of the hollow organ or a plurality of planes along a centerline which is formed by connecting the coordinates of the center of gravity of each cross section of the hollow organ,
wherein in the coordinate transformation step, the coordinate transformation is performed on each plane divided in the division step, and
in the generation step, the folded volume image is generated by combining the respective planes having the image information after the coordinate transformation.

10. The image processing method according to claim 8, further comprising:
a display step of generating a folded three-dimensional image by projecting the folded volume image generated in the generation step from an arbitrary viewing direction and displaying the folded three-dimensional image, 11. The image processing method according to claim 10.
wherein a range for the coordinate transformation in the coordinate transformation step is limited according to the folded three-dimensional image displayed in the display step.

12. The image processing method according to claim 8,
wherein the convex curved surface is at least one of a circle, an ellipse and an arbitrary curved surface which are adjacent to an outer surface of the hollow organ.

13. The image processing method according to claim 10, further comprising:
a three-dimensional moving image display step of generating a plurality of the folded three-dimensional images by performing the coordinate transformation in the coordinate transformation step while moving the convex surface sequentially along an outer surface of the hollow organ and displaying the plurality of folded three-dimensional images sequentially.

14. The image processing method according to claim 10. further comprising:
a surface deformation display step of generating a plurality of the folded three-dimensional images with different surface shapes at folded positions by performing the coordinate transformation using the coordinate transformation step by changing the shape of the convex surface sequentially or according to an operation of an operator and displaying the plurality of folded three-dimensional images sequentially.

\* \* \* \* \*